US00PP11302P

United States Patent [19]

Utecht

[11] Patent Number: Plant 11,302

[45] Date of Patent: Mar. 21, 2000

[54] GERANIUM PLANT NAMED 'FISEYE'

[75] Inventor: Angelika Utecht, Montabaur, Germany

[73] Assignee: Florfis AG, Binningen, Switzerland

[21] Appl. No.: 08/968,042

[22] Filed: Nov. 12, 1997

[51] Int. Cl.[7] ..... A01H 5/00

[52] U.S. Cl. ..... Plt./325

[58] Field of Search ..... Plt./87.12, 325, Plt./329

*Primary Examiner*—Howard J. Locker

*Attorney, Agent, or Firm*—Foley & Lardner

[57] ABSTRACT

A new and distinct cultivar of geranium named 'Fiseye', particularly characterized by the combined features of light violet flowers with large red macules; round, open, slightly semi-double flower shape; relatively small inflorescences; large, intense green leaves without zonation; medium plant habit in combination with good branching characteristics and short internodes, and medium early spring flower response.

1 Drawing Sheet

The present invention comprises a new and distinct cultivar of geranium, botanically known as *Pelargonium zonale*, and referred to by the cultivar name 'Fiseye'.

'Fiseye' is a product of a planned breeding program which had the objective of creating new geranium cultivars with bicolored flowers in combination with intense green foliage.

'Fiseye' was originated from a hybridization made by inventor Angelika Utecht in a controlled breeding program in Galdar, Gran Canaria, Spain in 1992. The female parent was the unpatented cultivar 'Icecrystal', characterized by light violet, semi-double flowers with rose-red to purple eyes, relatively large, light green foliage without zonation, and medium tall plant habit. The male parent of 'Fiseye' was the hybrid seedling no. 1257/3, characterized by its single light pink flowers with dark pink macules, and medium green foliage without zonation.

'Fiseye' was discovered and selected as one flowering plant within the progeny of the stated cross by Angelika Utecht in 1993 in a controlled environment in Galdar, Gran Canaria, Spain. The first act of asexual reproduction of 'Fiseye' was accomplished when vegetative cuttings were taken from the initial selection in Autumn 1993 in a controlled environment in Galdar, Gran Canaria, Spain, by, or under the supervision of, Angelika Utecht.

Horticultural examination of plants grown from these cuttings initiated in May, 1994 in Hillscheid, Federal Republic of Germany, and continuing thereafter, has demonstrated that the combination of characteristics as herein disclosed for 'Fiseye' are firmly fixed and are retained through successive generations of asexual reproduction.

'Fiseye' has not been observed under all possible environmental conditions. The phenotype may vary significantly with variations in environment such as temperature, light intensity and day length, without, however, any variation in genotype.

The following observations, measurements, and comparisons describe plants grown in Hillscheid, Federal Republic of Germany, under greenhouse conditions which approximate those generally used in commercial practice.

The following traits have been repeatedly observed and are determined to be basic characteristics of 'Fiseye', which in combination distinguish this geranium as a new and distinct cultivar:

1. Light violet main flower color with large red macules on petals.
2. Round, weakly semi-double flower type.
3. Compact semi-spherical inflorescences on relatively short peduncles.

4. Comparatively large, medium green leaves without zonation.
5. Medium tall plant habit, well-branched and with short internodes.
6. Medium spring flower response.

Of the many commercial cultivars known to the present inventor, the most similar in comparison to 'Fiseye' is the maternal parent 'Icecrystal'. Reference is made to Chart A which compares certain characteristics of 'Fiseye' to those same characteristics of 'Icecrystal'. In general comparison to 'Icecrystal', 'Fiseye' has a more intense flower color (main color as well as macules), more round flower shape with markings on both the upper and lower petals which are almost the same size, smaller inflorescences, and more intense green foliage.

CHART A

| | FISEYE | ICECRYSTAL |
|---|---|---|
| Main flower color, RHS: | 77 C | 77 D |
| Color of macules | 57 A | 66 B or lighter |
| Peduncles, length (cm) | 10.0 | 15.1 |
| Peduncles, color | medium green | reddish |
| Umbel, diameter (mm) | 75–80 | 90–105 |
| Foliage, color | medium green | light to medium |
| (R.H.S.) | 137 B–C | green about 143 C |

The accompanying color photographic drawing shows typical flower and foliage characteristics of 'Fiseye', with colors being as true as possible with illustrations of this type.

In the following description, color references are made to The Royal Horticultural Society Colour Chart. The color values were determined indoors from flowers grown in a greenhouse in May 1995 in Hillscheid, Germany.

Classification:

*Botanical.*—A hybrid of the species *Pelargonium zonale L'Hert.*

*Commercial.*—Zonal geranium, cv. 'Fiseye'.

Inflorescence:

*Umbel.*—Shape: Semi-spherical. Average diameter: 78 mm. Average depth: 50 mm. Peduncle length: 100 mm. Color of peduncle: light of medium green, R.H.S. 141 C–137 D. Pedicel length: 15 mm. Pedicel color: Green, R.H.S. 137 C-D, upper third may be reddish. Number of flowers per umbel: about 15–25.

*Corolla.*—Average diameter: 46 mm. Form: Weakly semi-double, round open. Number of petals: 5–9.

Number of petaloids: 0–1. Color (generally tonality from a distance of three meters): Light violet. Color of upper petals: 77 C. Color of lower petals: R.H.S. 77C. Markings of upper and lower petals: Large red macules, approximately 57 A. Color of lower surface of petals: 78 C-D. Color of sepals: Green. Number of sepals: 5.

*Bud.*—Shape: Elliptic. Size: short before unfolding, about 17 mm in length (without pedicel) and about 8 mm in width. Color (adaxial): Green R.H.S. 137C-D. Color (abaxial): Pink violet R.H.S. 72 C or lighter.

*Reproductive organs.*—Androecium: 5 fertile anthers; whitish filaments, yellow-orange pollen. Gynoecium: 5–6 lobed stigma, purple pink style and stigma. Seed set: No seed set observed.

*Spring flowering response period.*—In Hillscheid, Germany in 1995 plants had on average 0.9 flowers opened 11 weeks after planting of unrooted cuttings.

*Outdoor flower production.*—The flower count in 1994 in Hillscheid, Germany indicated 32 umbels per plant for May through August observation period.

*Durability.*—Good shatter resistance, good rain resistance.

Plant:

*Foliage.*—Form: Kidney-shaped. Margin: Bicrenated (very weak). Size of leaf: 110 mm. Color of upper surface: Medium green, approximately 137 B-C, glossy surface. Color of under surface: about R.H.S. 137 D. Color of zonation: No zonation. Tolerance of botrytis: Good.

*General appearance and form.*—Internode length: 5–10 mm. Branching pattern: 5.4 branches per plant (for 12-week-old plants). Height of plants: 30 cm (in September, for 35-week-old plants comprising foliage without inflorescences, measured from the surface of the soil to the top).

I claim:

1. A new distinct cultivar of geranium plant named 'Fiseye', as illustrated and described.

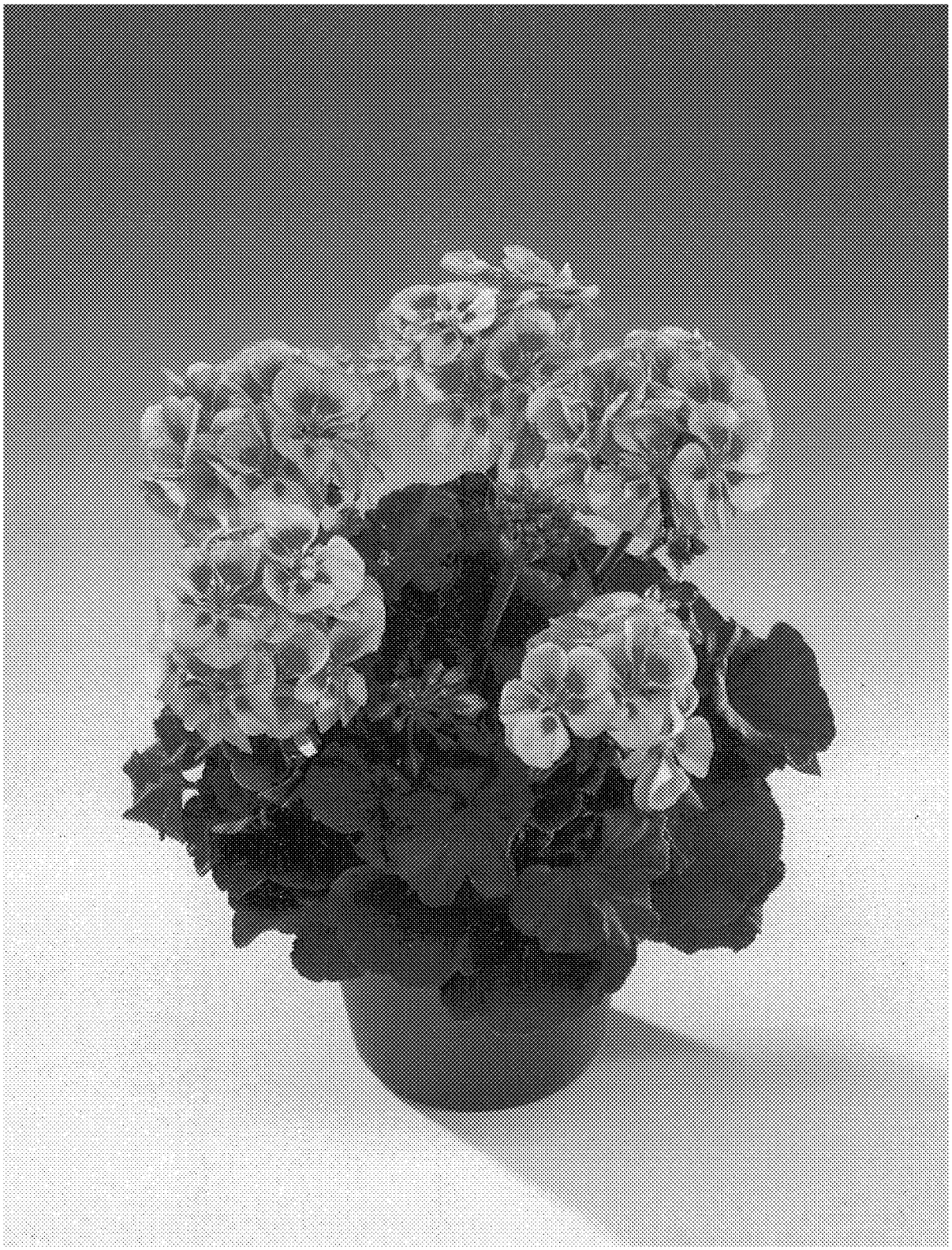

* * * * *